(12) United States Patent
Smith et al.

(10) Patent No.: US 7,904,150 B2
(45) Date of Patent: Mar. 8, 2011

(54) BIOFEEDBACK ELECTRONIC STIMULATION DEVICE

(75) Inventors: Timothy Brooks Smith, Dallas, TX (US); Tammy Jane Smith Lahutsky, Plano, TX (US); Woodrow W. Baker, II, Nacogdoches, TX (US); Terryl Everett Biggs, Addison, TX (US)

(73) Assignee: Avazzia, Inc., Dallas, TX (US)

( * ) Notice: Subject to any disclaimer, the term of this patent is extended or adjusted under 35 U.S.C. 154(b) by 238 days.

(21) Appl. No.: 12/350,566

(22) Filed: Jan. 8, 2009

(65) Prior Publication Data

US 2009/0112284 A1 Apr. 30, 2009

Related U.S. Application Data

(62) Division of application No. 11/203,387, filed on Aug. 12, 2005, now Pat. No. 7,509,165.

(60) Provisional application No. 60/601,075, filed on Aug. 12, 2004.

(51) Int. Cl.
*A61B 5/04* (2006.01)

(52) U.S. Cl. .................... 607/2; 607/50; 607/62

(58) Field of Classification Search .......... 600/547; 607/2, 6, 42, 45, 50, 51, 52, 62, 68, 72, 73
See application file for complete search history.

(56) References Cited

U.S. PATENT DOCUMENTS

| | | | |
|---|---|---|---|
| 4,105,017 A | 8/1978 | Ryaby et al. |
| 4,112,923 A | 9/1978 | Tomecek |
| 4,266,532 A | 5/1981 | Ryaby et al. |
| 4,266,533 A | 5/1981 | Ryaby et al. |
| 4,998,532 A | 3/1991 | Griffith |
| 5,014,699 A | 5/1991 | Pollack et al. |
| 5,304,207 A | 4/1994 | Stromer |
| 5,723,001 A | 3/1998 | Pilla et al. |
| 5,974,342 A | 10/1999 | Petrofsky |
| 6,221,095 B1 | 4/2001 | Van Zuylen et al. |
| 6,249,698 B1 | 6/2001 | Parris |
| 6,745,078 B1 | 6/2004 | Buchner |
| 7,198,633 B1 | 4/2007 | Starwynn |
| 7,503,927 B1 | 3/2009 | Vetanze |
| 2004/0267333 A1 | 12/2004 | Kronberg |
| 2007/0129759 A1 | 6/2007 | Colthurst |

*Primary Examiner* — Carl H Layno
*Assistant Examiner* — Gary A Porter, Jr.
(74) *Attorney, Agent, or Firm* — Howison & Arnott, L.L.P.

(57) ABSTRACT

A biofeedback electronic stimulation device includes a processor for generating a first control signal and a plurality of second control signals responsive to at least one input signal. Transformer circuitry generates a stimulation signal including packets of at least one pulse responsive to the first control signal. Pulse circuitry configures the at least one pulse in the packet to a selected one of a plurality of configurations responsive to the plurality of second control signals. Output electrodes apply the at least one pulse in the packet to a user and detector circuitry detects zero crossings of the at least one pulse in the packet. The processor further causes generation of an indicator responsive to the detected zero crossings.

12 Claims, 8 Drawing Sheets

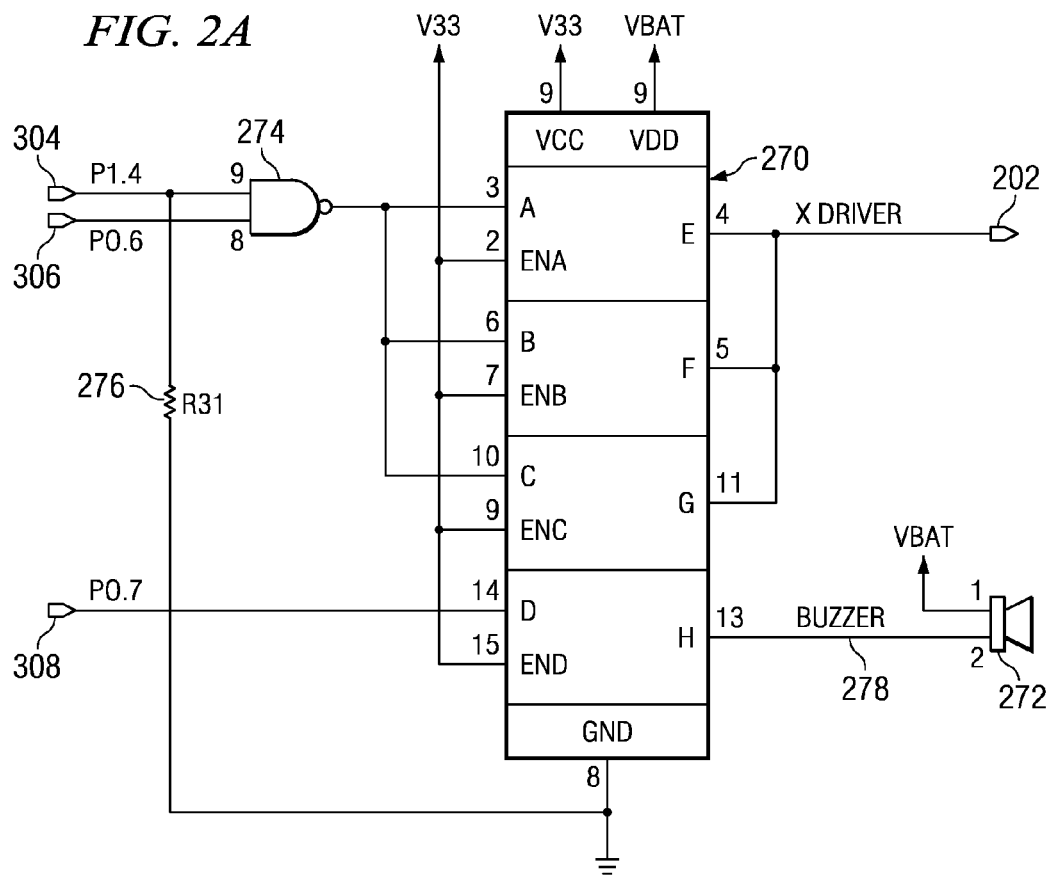
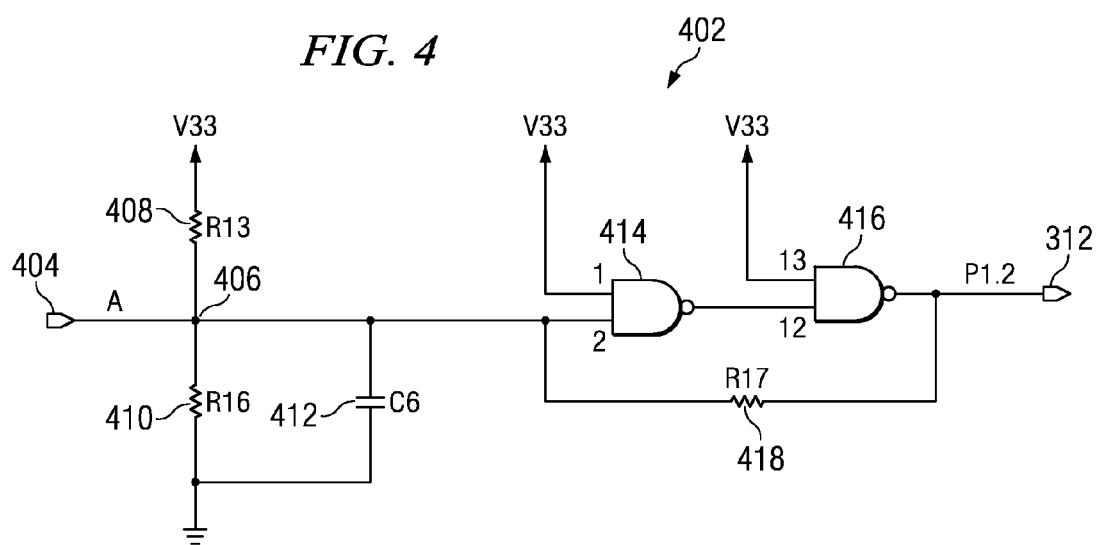

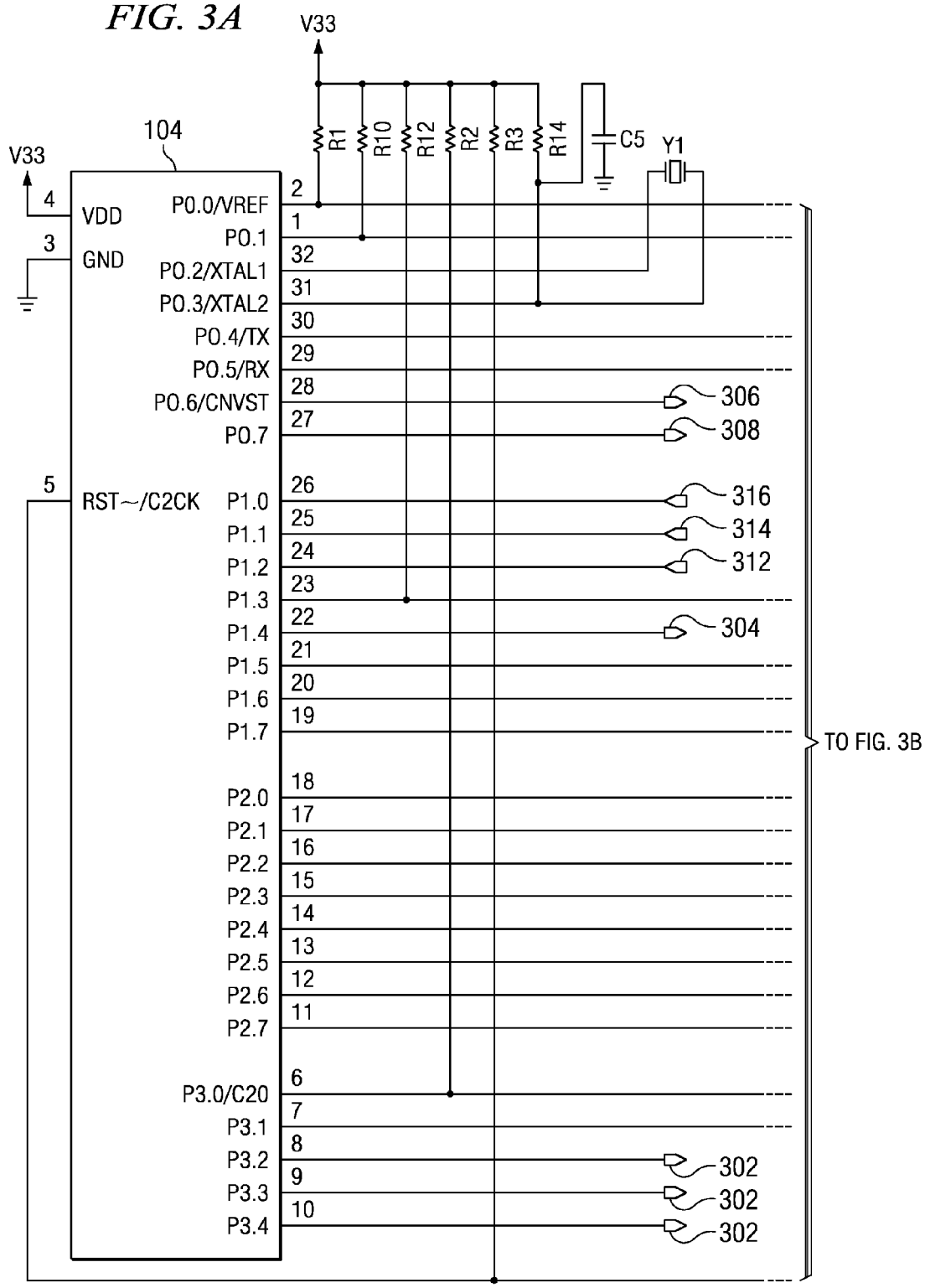

BIOFEEDBACK ELECTRONIC STIMULATION DEVICE

CROSS-REFERENCE TO RELATED APPLICATIONS

This application is a Divisional of U.S. patent application Ser. No. 11/203,387, now U.S. Pat. No. 7,509,165, filed on Aug. 12, 2005, which claims priority to U.S. Provisional Patent Application Ser. No. 60/601,075, filed on Aug. 12, 2004 and entitled "BIOFEEDBACK ELECTRONIC STIMULATION DEVICE," which is incorporated herein by reference.

TECHNICAL FIELD OF THE INVENTION

The present invention relates to pain management systems, and more particularly, to biofeedback electronic stimulation devices.

BACKGROUND OF THE INVENTION

There are many people with injuries and ailments that may be treated by electrical energy. Examples include sprained ankles, carpal tunnel syndrome, arthritis, and numbness of extremities like neuropathy, stroke and neurological conditions such as ADD and macular degeneration. These are all ailments that the human body must work to recover from. They are not viruses or infections or any chemically related ailment. These are not instances where surgery has proven effective, such as reattaching bones or ligaments or other body parts or clearing arteries.

Energetic medicine addresses these energy related ailments. There has been much research into energetic medicine and the way the body's electric and nervous system works dating back to the 1900s. Devices have been developed, such as the Rife machine, Beck's Box, infrared light therapies, and magnetic therapies used in energetic medicine. There are diagnostic tools such as MEAD machines, which measure resistance in the body's energetic pathways called energy meridians. There are also treatment machines in the category in TENS and electronic acupuncture. With respect to the use of machinery based upon TENS strategy, most of these devices utilize electronic stimulation to mask the pain of a user rather than to physically assist the body to recover from a particular injury. Thus, there is a need for devices that actively assist the body in healing from particular types of injuries using electrical energy.

SUMMARY OF THE INVENTION

The present invention disclosed and claimed herein, in one aspect thereof, comprises a biofeedback electronic stimulation device. The device has a user interface enabling a user to select at least one input signal. A processor within the device generates a first control signal and a plurality of second control signals responsive to the at least one input signal. Transformer circuitry generates a stimulation signal including packets containing at least one pulse responsive to the first control signal from the processor. Pulse circuitry configures at least one pulse in the packet to a selected one of a plurality of configurations responsive to the plurality of second control signals. The stimulation signal is applied to the body of a user using output electrodes. Detector circuitry detects zero crossings of the at least one pulse in the packet of the stimulation signal, and the processor generates an indicator responsive to the detected zero crossings.

BRIEF DESCRIPTION OF THE DRAWINGS

For a more complete understanding of the present invention and the advantages thereof, reference is now made to the following description taken in conjunction with the accompanying Drawings in which:

FIG. 2a is a schematic diagram of the level translator circuitry;

FIG. 3a-3b is a schematic diagram of the microcontroller of the device;

FIG. 4 is a schematic diagram of the detector circuit of the device;

DETAILED DESCRIPTION OF THE INVENTION

Figure 1:
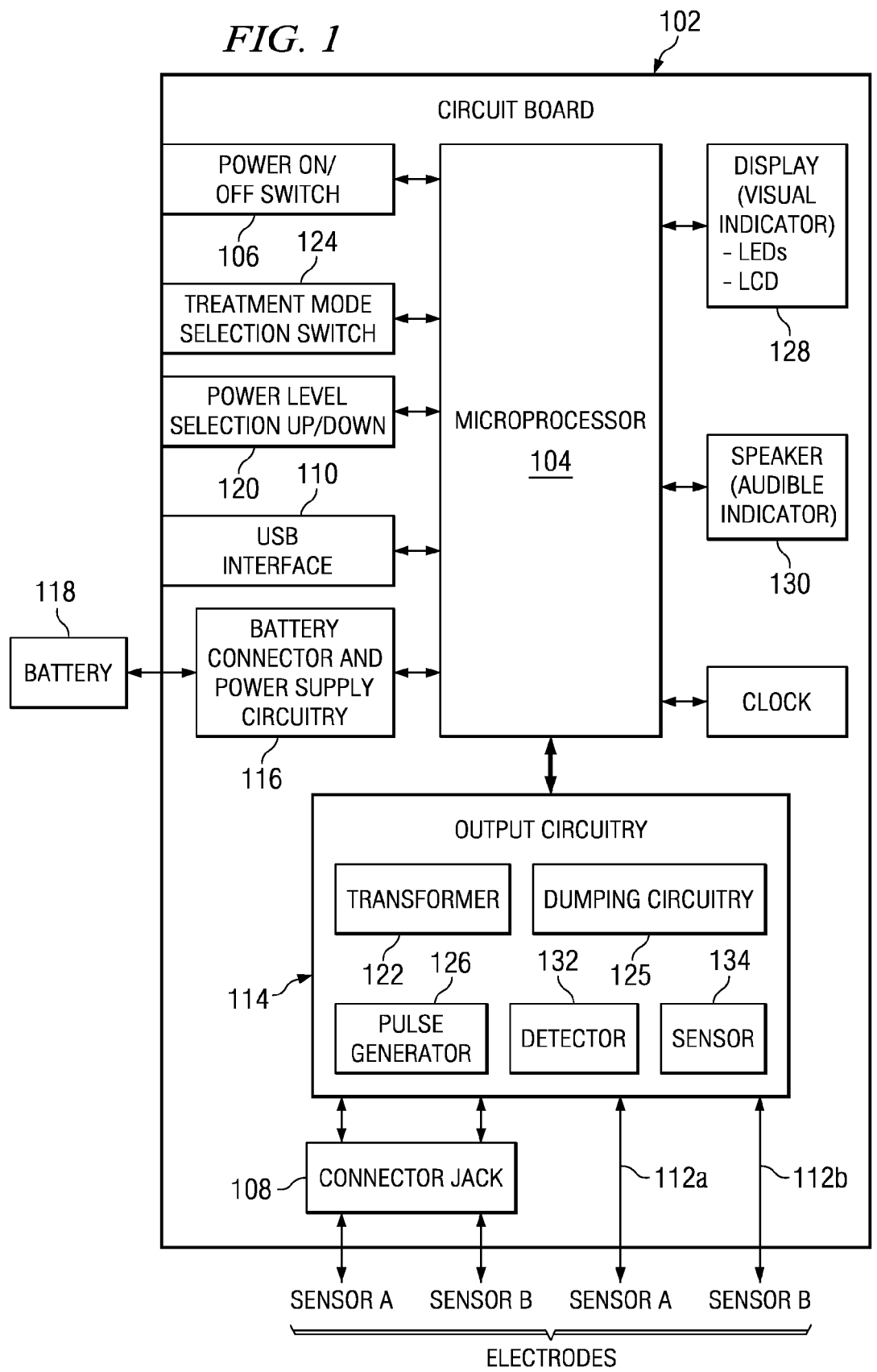
FIG. 1 is a block diagram of the biofeedback electronic stimulation device of the present invention.

Referring now to the drawings, wherein like reference numbers are used herein to designate like elements throughout the various views, embodiments of the present invention are illustrated and described, and other possible embodiments of the present invention are described. The figures are not necessarily drawn to scale, and in some instances the drawings have been exaggerated and/or simplified in places for illustrative purposes only. One of ordinary skill in the art will appreciate the many possible applications and variations of the present invention based on the following examples of possible embodiments of the present invention.

Referring now to FIG. 1, there is illustrated a block diagram of the biofeedback electronic stimulation device of the present invention. The device includes a circuit board 102 for containing each of the electronic components. The controlling portion of the device consists of a microprocessor 104. The microprocessor 104 contains a set of stored instructions for controlling the operation of the biofeedback device. The microprocessor 104 in conjunction with other components of the device which will be discussed herein below generate output pulse packets for application to an individual's body. The microprocessor 104 is interconnected with a number of components on the circuit board 102 from which the microprocessor 104 receives inputs from and provides outputs to. An on/off switch 106 provides the user with the ability to turn the entire biofeedback electronic stimulation device on and off. The on/off switch 106 may comprise a standard push button switch or a conventional two position switch in order to place the device in powered and non-powered states. A connector jack 108 enables external probes to be connected to the biofeedback electronic stimulation device. The device also includes a USB port 110 to enable universal serial bus connections to the microprocessor 104. Through the USB connection 110, a USB communications cable may be connected to enable USB communications between the microprocessor 104 and an external device.

A pair of electrodes 112 provide a stimulation signal from the output circuitry 114 and provide a connection point between the biofeedback electronic stimulation device and a body of a user. The output electrodes 112 connect the device to a point on a body of a user. The pair of electrodes 112 additionally provide an input for measuring a body's response to the applied electric signals through the electrodes 112. A connector 116 enables a battery 118 to be interconnected to the biofeedback electronic stimulation device to power the microcontroller 104 and associated circuitry. The power level selector 120 enables a user to adjust the power level applied to a transformer 122 within the output circuitry 114 by the microprocessor 104 to various levels. The applied power level alters the strength of the stimulation signal output from electrodes 112 to a user's body.

Treatment selector switch 124 selects the particular mode of operation for the biofeedback electronic stimulation device. The selected treatment mode from switch 124 provides an indication to the microprocessor 104 of a particular operating mode. The microprocessor 104 configures the pulse generator circuitry 126 to provide a desired pulse output according to the selected mode of operation. A series of display LEDs and/or LCDs 128 provide a visual indication of the power level of the device, the mode of operation or other device status. Additionally, a speaker 130 may be used to provide audible indicators to a user of various operating conditions. Various visual and audible indications are provided by the LEDs and LCDs 128 or the speaker 130. These instructions include a mode indication, a power level indication, a battery power indication, a sensor connection indication, a body response status, a time status, body measurement readings, USB interface status, instructional information, treatment status, or diagnosis information. The transformer circuit 122 is energized by signals from a pulse generator circuit 126.

The output circuitry 114 is connected to and controlled by the microprocessor 104 to generate output pulses in a stimulation signal through the electrodes 112. The output circuitry 114 also receives feedback signals from the electrodes 112 to control the operation of the microprocessor 104. A transformer 122 generates a signal including packets of one or more pulses responsive to removal of an applied current from the transformer 122 controlled by the microprocessor 104. The transformer circuit 122 is energized by signals from a pulse generator circuit 126. The output pulses provided from the transformer may be clamped by damping circuitry 125. The various characteristics of the pulse generated by the pulse generator 126 are controlled responsive to control inputs from the microprocessor 104. A detector circuit 132 is responsible for detecting the zero crossing of the pulse signals provided at the electrodes 112. The time between the zero crossing is used by the microprocessor 104 to determine when the device may be removed from the body. The sensor circuit 134 provides the measurements for the zero crossings.

Figure 2:
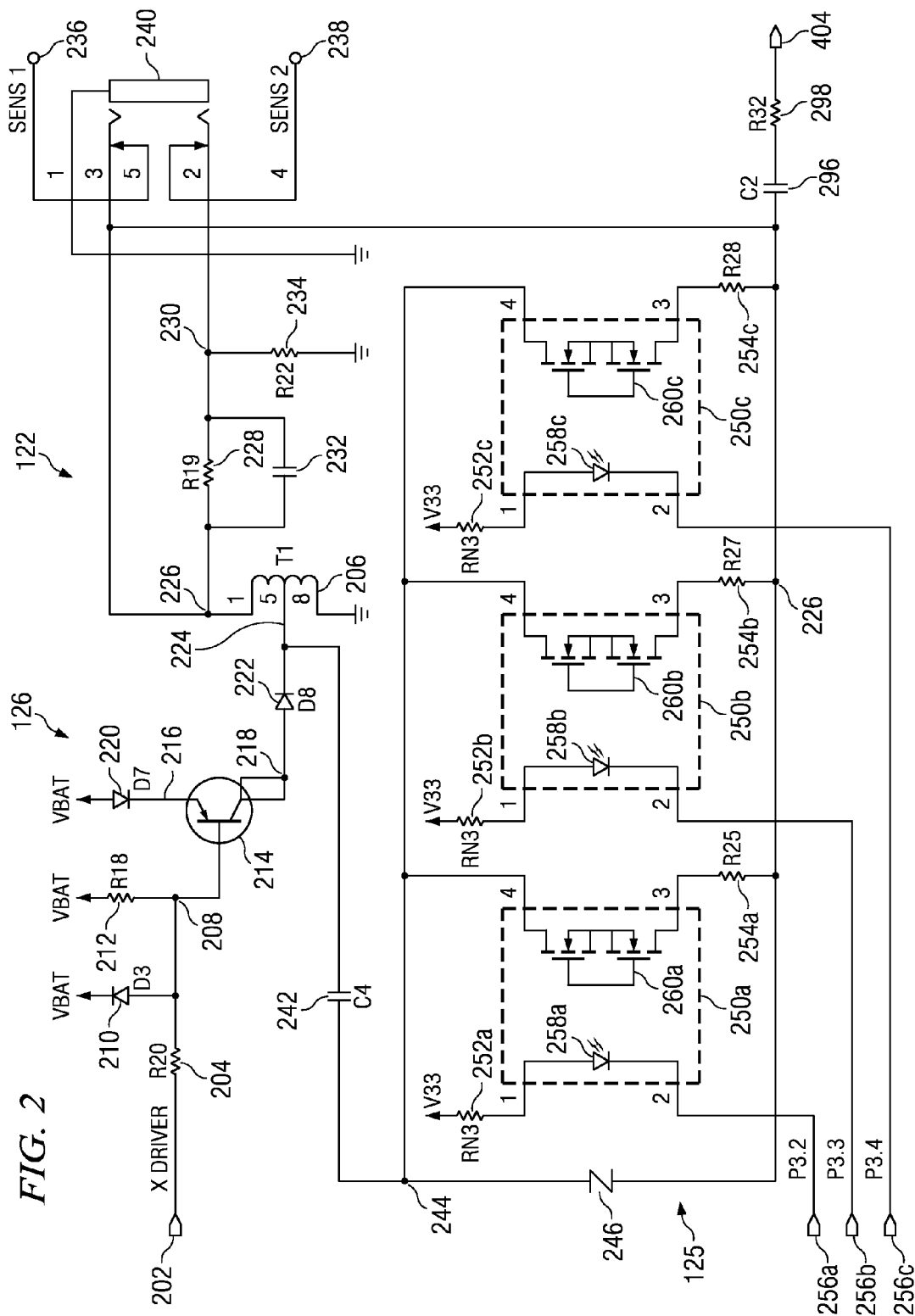
FIG. 2 is a schematic diagram of the transformer circuit and associated transformer shunt.

Referring now to FIG. 2, there is illustrated a schematic diagram of the transformer circuitry 122 the pulse generator circuitry 126 and the damping circuitry 125. A charging current is applied at input 202 to resistor 204. The charging current is provided from the level translator circuit 270 (FIG. 2a) under control of the microprocessor 104. The charging current provides energy to a transformer 206 for generating the stimulation signal. Resistor 204 is also connected to node 208. An anode of diode 210 is connected to node 208 and the cathode of diode 210 is connected to VBatt. A resistor 212 is connected between VBatt and node 208. The base of transistor 214 is connected to node 208 and the emitter-collector path of transistor 214 is connected between node 216 and node 218. A diode 220 has its anode connected to VBatt and its cathode connected to node 216. A diode 222 has its anode connected to node 218 and its cathode connected to a center tap 224 of transformer 206. One side of transformer 206 is connected to ground, and the opposite side of transformer 206 is connected to node 226. When a charging current is applied to node 202, transistor 214 is turned on causing a current to be applied to the center tap 224 of transformer 206 by the pulse generator circuitry 126 and begin energizing the transformer.

A resistor 228 is connected between node 226 and node 230. In the preferred embodiment, the resistor 228 has a value of 150 kilo ohms. A capacitor 232 is in parallel with resistor 228 between nodes 226 and 230. In a preferred embodiment, the capacitor 232 has a value of 500 picofarads. This capacitor can eliminate the need for the damping device 246 discussed below by limiting the amplitude of pulses generated by the transformer 206. A resistor 234 is connected between node 230 and ground. Sensor one output 236 is connected to node 226. Sensor two output 238 is connected to node 230. An external sensor 240 is connected between node 226 and node 230. The transformer circuitry 122 is interconnected with the damping circuitry 125 via a capacitor 242. The capacitor 242 is located between the center tap 224 and node 244 of the damping circuitry 125.

The damping circuitry 125 includes a clamping device 246 located between node 244 and node 226. The clamping device 246 prevents the pulses generated when the current is released from the transformer 206 from exceeding a particular amplitude. In a preferred embodiment, the clamping device 246 comprises a bidirectional rectifying diode. The remaining portion of the pulse generator circuitry 126 consists of a transformer shunt enabling the load applied across the transformer 206 to be adjusted by switching resistances into and out of the load applied to the transformer 206. The transformer shunt consists of three relays 250, which switch a resistor load 254 into and out of the circuit. Each relay 250 has four connections. A first connection is connected to a resistor 252 that is also connected to the system voltage. The relays 250 have a second connection to a load resistor 254 connected between the relay and node 226. Another connection of the relay 250 is connected to control inputs 256 from the microprocessor 104. A light emitting diode 258 is connected between the connection to resistor 252 and the input connected to the control input 256. The light emitting diode 258, when lit actuates a pair of photo sensitive transistors 260 connected between third and fourth inputs of the relay 250. When a control signal is applied to input 256 of one of the relays 250, the light emitting diode 258 causes the actuation of the photo sensitive transistor pair 260, which switches the resistor 254 of the transformer shunt across the transformer 206. As can be seen, there are three relays 250 enabling eight different combinations of the resistors 254 to be switched across the transformer 206 responsive to control signals applied to lines 256a through 256c. Using these various combinations of relays 250, the microprocessor 104 controls the shape and configuration of the packet of pulses output by the transformer in a number of fashions which will be discussed more fully herein below such that the stimulation signal may be configured in a number of desired modes responsive to user inputs. While only three relays 250 are described with respect to the present embodiment, any number of relays 250 may be used.

FIG. 2a illustrates the level translator circuit 270 for generating the transformer charging signal on line 202. The transformer charging signal is generated by the level translator 270 responsive to control inputs 304 and 306 applied to first and second inputs of a NAND gate 274. The output of the NAND gate 274 is provided to three separate inputs of the level translator 270. A resistor 276 is connected between the input of NAND gate 274 connected to control input 304 and ground. An audio speaker 272 is connected to receive an audio signal from the level translator circuit 270 on line 278 responsive to a control input 308 from the microcontroller 104.

Figure 3B:
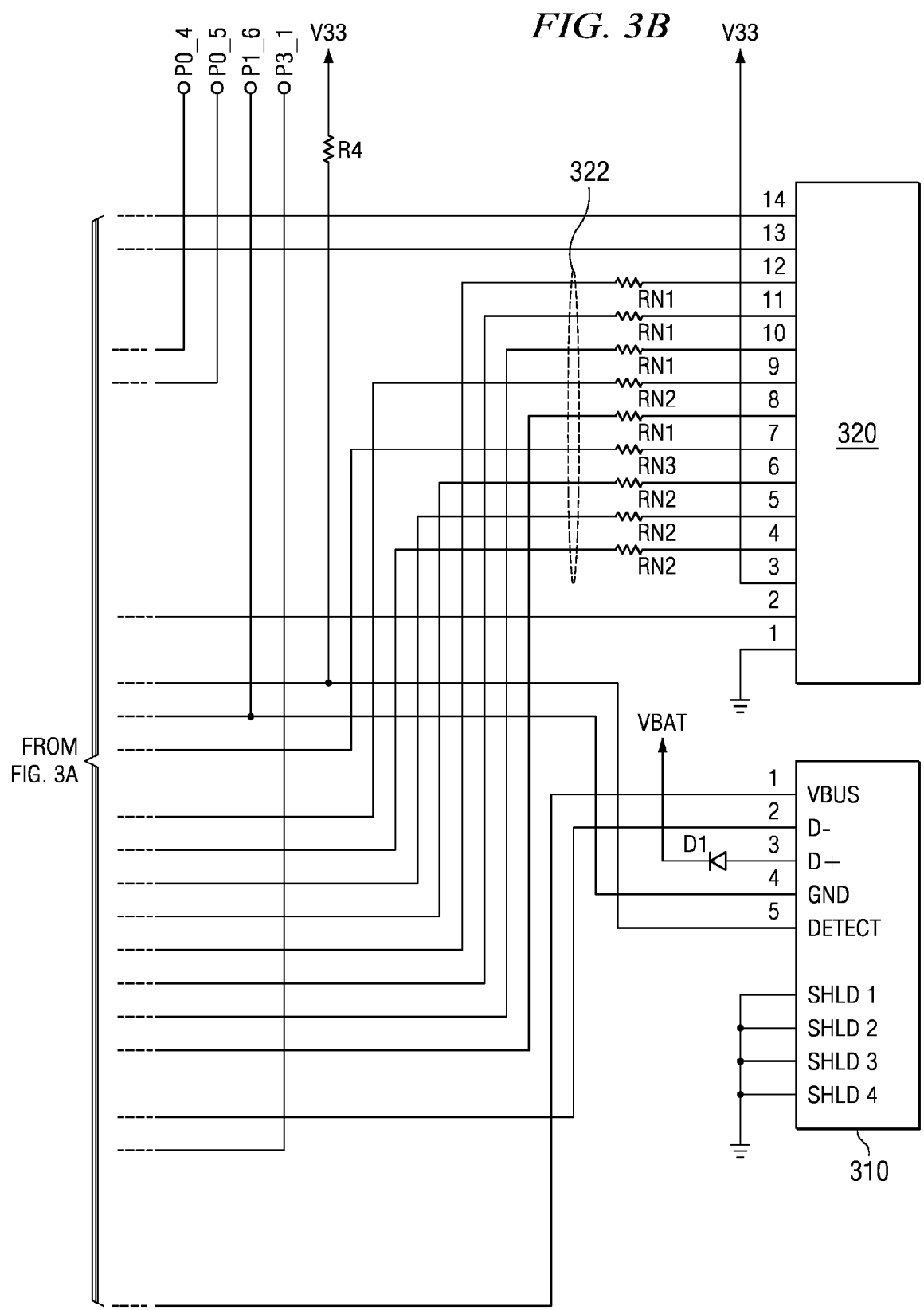

Referring now to FIGS. 3a-3b, there is illustrated the microprocessor 104 for controlling the biofeedback electronic stimulation device described herein. The microprocessor 104 provides three control outputs 256 for controlling the transformer shunt relays 250 described previously. As described herein above, these signals enable the control of the configuration of the pulse packages generated from the transformer 206. Control outputs 304, 306 and 308 provide control signals to the level translator 270 to control the provision of the transformer charging signal on output 202 responsive to control signals 304 and 306 and to control the audio output to speaker 272 via control output 308. An LED circuit 320 receives a number of control outputs 322 from the microprocessor 104 to provide various visual indicators to the user of the biofeedback electronic stimulation device.

Control input 312 receives an input control signal from the detector module 132 as described in FIG. 4. The detector module 132 is responsible for determining the number of zero crossings for pulse signals generated within signal packets provided by the transformer 206. The input 404 of the detector module 132 is connected to node 226 on one side of the transformer 206 through capacitor 296 and resistor 298. The input 404 is connected to node 406 of the detector 132. A resistor 408 is connected between node 406 and system power. A second resistor 410 is connected between node 406 and system ground. A capacitor 412 is in parallel with resistor 410 between node 406 and ground. A first input of NAND gate 414 is connected to node 406. The second input of NAND gate 414 is connected to system power. The output of NAND gate 414 is connected to a first input of NAND gate 416. The second input of NAND gate 416 is connected to system power. The output of NAND gate 416 is connected to control input 312 from the microprocessor 104. A resistor 418 is connected between the input of NAND gate 414 connected to node 406 and to the output of NAND gate 416. Control inputs 314 and 316 are connected to a battery sensor circuit.

The processor may use the control signals to control a number of processes within the device. The processor may control the amount of damping applied to each pulse. The processor may also control the stimulation pulse applied by the pulse generator to the transformer and the power or pulse width of the stimulation pulse. Control signals may also be generated responsive to the analysis of patterns in a response signal from the body and altered in real time. The altered control signals may generate a pulse that drives the response from the body to a desired outcome. The analysis may also be communicated to the user or a data collection apparatus along with any derived information.

Figure 5:
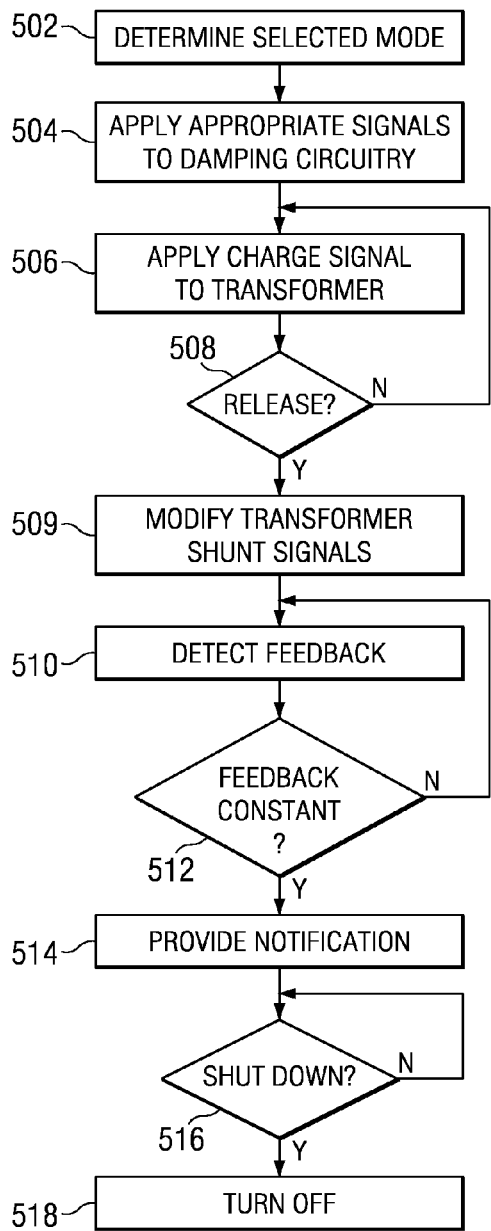
FIG. 5 is a flow diagram illustrating the manner in which the control processor operates within the device to provide control signals.

The generation of the control signals by the microprocessor 104 is more fully described with respect to the flow diagram illustrated in FIG. 5. Initially, at step 502, the microprocessor 104 determines the selected mode of operation of the biofeedback electronic stimulation device responsive to inputs received from the treatment mode selection switch 124 and the power level selection switch 120. From the selected mode and power level, the microprocessor 104 determines the appropriate control signals to be applied to the relays 250 of the damping circuitry 125 and applies these control signals at step 504. The microprocessor 104 also determines and applies at step 506 the appropriate control signals 125 to charge the transformer 206 via the level translator 270. This is accomplished by applying the appropriate control signals at step 506 to the level translator circuit 270. The charging signal is continuously applied to the transformer 206 at step 506 until inquiry step 508 determines a release point has been received responsive to the applied control signal from the microprocessor 104.

Once inquiry step 508 determines to release the charging signal, the microprocessor 104 modifies the control signals applied to the transformer shunt at step 509 to modify the stimulation signal as desired. In some embodiments, the control signals applied to the transformer shunt may remain constant and the control signals will not be modified at step 509. The microprocessor 104 next monitors the feedback provided from the electrodes 112 that are providing the electronic stimulation signal to the body of a user. The specifics of the feedback detection will be more fully discussed with respect to FIG. 6. Inquiry step 512 determines if the feedback received by the microprocessor 104 has remained constant for a selected period of time. If not, the microprocessor 104 continues to detect the feedback at step 510. Once inquiry step 512 determines that the feedback is constant for a selected period of time, some type of notification is provided at step 514 to the user of the biofeedback electronic stimulation device. This notification may take the form of an audio indicator, such as a beep played through the speaker 272 or some type of visual indicator through one of the LEDs or LCD displays 128. The microprocessor 104 then monitors for a shut down indication by the user powering off the device at inquiry step 516. Inquiry step 516 continues to monitor for some type of shut down signal until it is received. Upon receipt of a shut down signal, the microprocessor 104 turns off the device at step 518.

Figure 6:
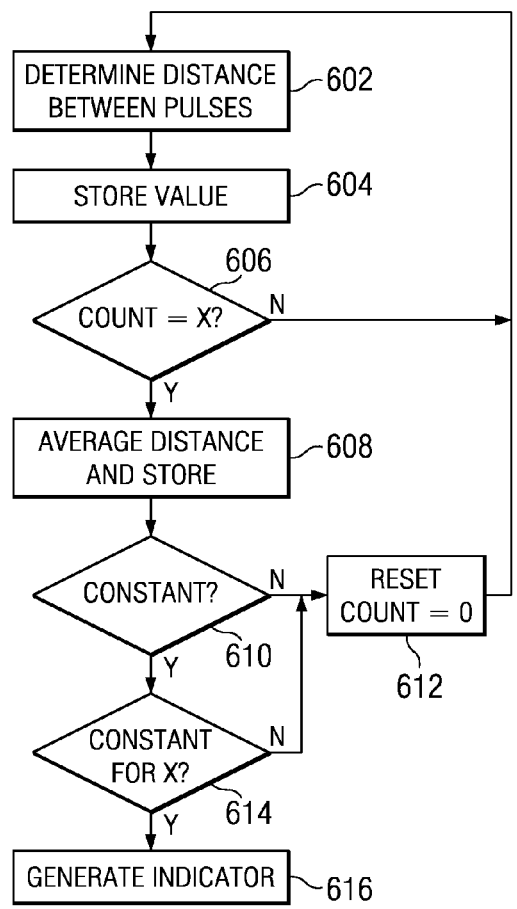
FIG. 6 is a flow diagram illustrating the feedback control loop of the biofeedback electronic stimulation device.

Referring now to FIG. 6, there is illustrated the manner in which the microprocessor 104 monitors the feedback from the electrodes 112 which are applying the electronic stimulation signal to an individual's body and detecting feedback from the body. The feedback determined by the microprocessor 104 comprises a determination of the time between zero crossings of the electronic stimulation signal. The time between the zero crossings of the pulses will alter based upon the resistance provided by the body to which the device has been attached. As the resistance in a person's body decreases, the time between zero crossings of the pulses of a packet will alter. Once the resistance is steady, the time between zero crossings of the pulses will remain constant and the treatment regimen may be stopped.

Once the time between the zero crossings of pulses is determined at step 602, this time value is stored within a memory associated with the microprocessor 104 at step 604. Inquiry step 606 determines if a count value is equal to a predetermined value that is used for averaging a number of time values. If not, control passes back to step 602. Once the appropriate number of time values have been stored and count is equal to the preselected value at inquiry step 606, the average time between the zero crossings of pulses may be determined at step 608. This value may be compared with a previously determined value at inquiry step 610 to determine if the determined average time value is constant. If the determined average time value is not constant, count is reset to zero at step 612 and control passes back to step 602. If it is determined that the stored time value is constant with a previously stored time value, inquiry step 614 determines if the successive number of average time values have been constant for a selected period Y. If not, count is reset to zero and control returns to step 602. Once the average time values have been constant for a selected period of time as determined at inquiry step 614, an indicator is generated to the user indicating the device may be shut down at step 616. In an alternative embodiment, the indicator could cause the device to automatically shut down rather than waiting for a user provided shut down signal.

Figure 7:
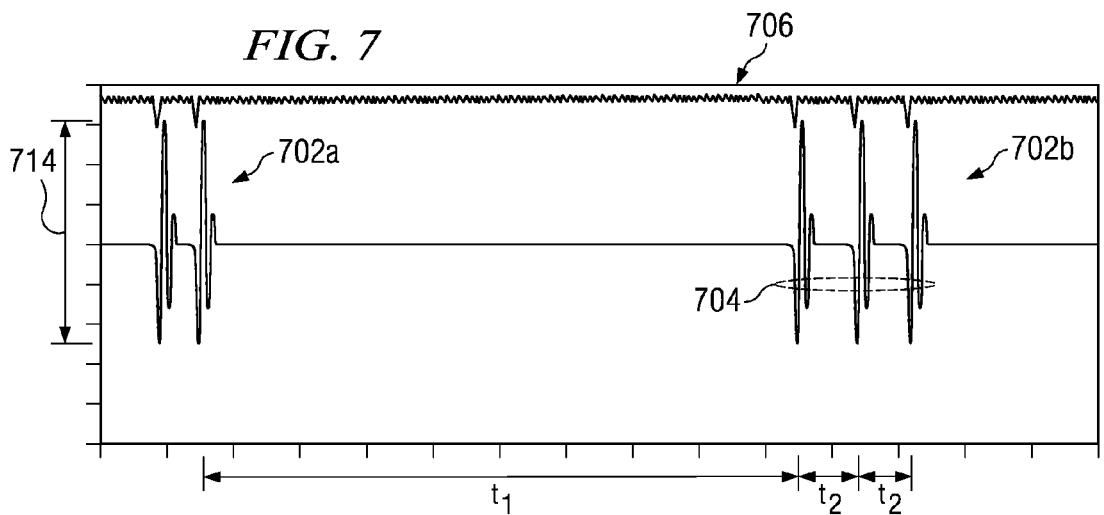
FIG. 7 illustrates the stimulation signal generated by the biofeedback electronic stimulation device, and the various manners in which the packets and pulses may be controlled.

Referring now to FIG. 7, the control values provided to the transformer shunt circuitry and to the level translator for the generation of the transformer charging signal may be used to configure packets 702 of pulses 704 which are transmitted in an electronic stimulation signal 706. Using the control signals, the packets 702 of pulses 704 are controlled in a number of manners. In one embodiment, a time t1 between a first packet 702a and a second packet 702b may be controlled using the control signals applied to the level translator circuit 270. The time t1 may be varied between adjacent packets or held constant. The microprocessor 104 may also control the number of pulses 710 located within a particular packet 702. The number of pulses 710 may be randomly varied between packets, gradually increased/decreased between packets or maintained constant. The size of the packet 702 may be extended or reduced by altering the number of pulses 704 within a packet 702 through use of the applied control signals to the pulse generation circuitry 126. The pulses may be varied from any number from 1-n. Within the stimulation signal the size of packets 702 may be varied or constant.

The microprocessor 104 may also control the time t2 between adjacent pulses 704 of a packet 702. This would be an alternative way for increasing or decreasing the size of a particular packet 702 by altering the time t2 between pulses 204 rather than changing the number of pulses per packet 710 as described previously. The time t2 may also be varied in any number of desired fashions. The time t2 between pulses may also be controlled using the control signals to the pulse generation circuitry 126. Additionally, the pulses 704 may be damped such that the amplitude 714 may be increased or decreased to change the magnitude of the pulses 704 provided within the electronic stimulation signal 706. The amplitude 714 is also controlled through the damping circuitry 125 and may be done with a combination of the relays 250 in the damping circuitry 125.

Figure 8A:
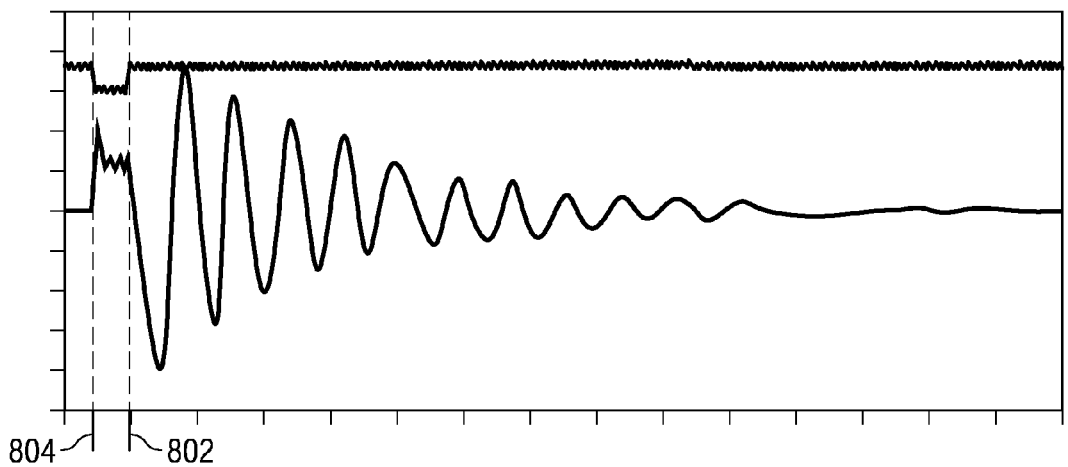
FIGS. 8a-8d illustrate various output signals of the biofeedback electronic stimulation device.
Figure 8B:
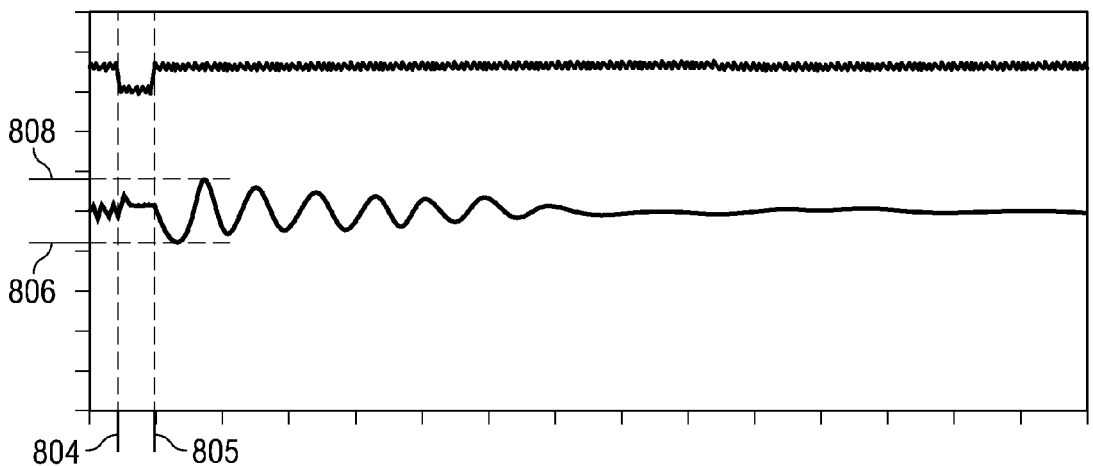
Figure 8C:
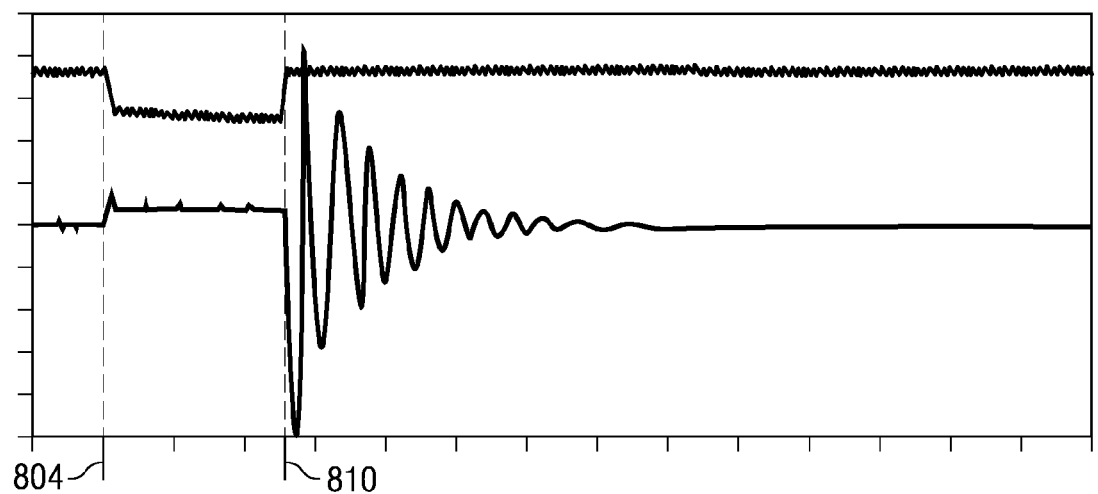

Referring now to FIGS. 8a through 8d, there are illustrated a number of pulse waveforms that illustrate the variety of outputs that may be achieved from the biofeedback electronic stimulation device described herein above. FIG. 8a illustrates a first pulse wherein the charging signal has been applied for a medium amount of time and released from application to the transformer at point 802. The output of the transformer begins the fly back oscillation mode creating the oscillations in the positive and negative directions with a steadily decreasing magnitude for the oscillation. The time period that the charging signal is applied between 804 and 802 controls the amplitude of the modulations of the output. By varying the release point 802, the amplitude of the output pulse may be increased or decreased. A situation wherein the amplitude of the output pulse is decreased is illustrated in FIG. 8b. In this figure, the charging time is held between points 804 and point 805. Due to the shorter magnitude of the application of the charging signal, the amplitude of the oscillation of the output signal between 806 and 808 is decreased. Referring now to FIG. 8c, there is illustrated a situation wherein the charging signal is applied between points 804 and 810 for a longer period of time, causing the amplitude of the output pulse to increase.

Figure 8D:
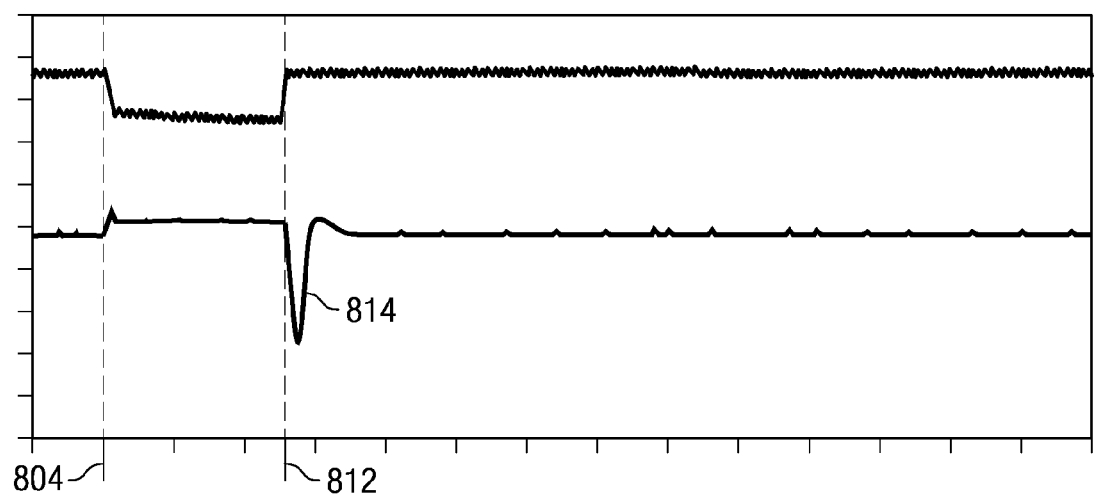

In addition to controlling the amplitude of the output by controlling the release point of the charging signal to the transformer, the damping circuit may be used to control the output pulse in the manner illustrated in FIG. 8d. In this case, the charging signal is applied between points 804 and 812. In this case, the output signal generates a single oscillation 814 in the negative direction that then approaches zero rather than oscillating in the positive direction. This may be achieved by applying the appropriate load across the output of the transformer using the damping circuitry 125.

Therefore, using the above-described device, a user may strategically apply an electronic stimulation signal to specific parts of their body and by the use of mode selection buttons, may control the configuration of the packets of pulses applied to their body. The pulses may be adjusted in any of the fashions discussed herein above.

It will be appreciated by those skilled in the art having the benefit of this disclosure that this invention provides an electronic stimulation device for providing healing signals to a person's body. It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

What is claimed is:

1. A biofeedback electronic stimulation device comprising:
    a user interface for providing at least one input signal;
    a processor for generating a first control signal and a plurality of second control signals responsive to the at least one input signal;
    a pulse generator circuit for generating a charge current responsive to the first control signal;
    a transformer for generating a stimulation signal including packets of at least one pulse responsive to the charge current;
    damping circuitry for configuring the at least one pulse in the packets to a selected one of a plurality of configurations responsive to the plurality of second control signals;
    output electrodes for applying the stimulation signal to a user;
    detector circuitry for detecting zero crossings of the at least one pulse in the packet of the stimulation signal;
    an audio indicator for providing an audio indication to cease application of the stimulation signal responsive to a third control signal from the processor;
    a visual indicator for providing a visual indication of at least one mode of operation of the device responsive to the at least one input signal;
    wherein the processor further causes generation of an indicator responsive to the detected zero crossings; and
    wherein the processor further configures a spacing between the packets of the stimulation signal, a number of pulses in the packets of the stimulation signal, a spacing between the pulses in the packets of the stimulation signal, and a damping of the pulses in the packets of the stimulation signal.

2. The biofeedback electronic stimulation device of claim 1, wherein the spacing between packets of the stimulation signal may be varied between each packet.

3. The biofeedback electronic stimulation device of claim 1, wherein the number of pulses in the packets of the stimulation signal vary between the packets.

4. The biofeedback electronic stimulation device of claim 1, wherein the spaces between pulses may be altered between packets of the stimulation signal.

5. The biofeedback electronic stimulation device of claim 1, wherein the microprocessor measures an average time between zero crossings responsive to occurrence of a selected number of detected zero crossings and generates the indicator when the average time between zero crossings is equal for a predetermined number of times.

6. The biofeedback electronic stimulation device of claim 1, further including a universal serial bus connector providing an external connection to the processor.

7. The biofeedback electronic stimulation device of claim 1, wherein the at least one input signal selects one of a plurality of modes of operation, each mode of the plurality of modes of operation having a selected first control signal and a selected plurality of second control signals associated therewith.

8. The biofeedback electronic stimulation device of claim 1, wherein the processor further controls an amount of damping applied to each pulse.

9. The biofeedback electronic stimulation device of claim 1, wherein the processor further varies a power of stimulation pulse applied to the transformer by the pulse generator circuit.

10. The biofeedback electronic stimulation device of claim 1, wherein the controller analyzes patterns in response signals received from a body of a user and based on detected patterns alters the control signals in real time.

11. The biofeedback electronic stimulation device of claim 10 wherein the analysis of the body response signals may be used to alter the controlling parameters of the pulse such that the response of the body is driven toward a desired outcome.

12. The biofeedback electronic stimulation device of claim 11 wherein the analysis of the body response signals further may cause additional derived information to be communicated to the user or to a data collection apparatus.

* * * * *